United States Patent [19]

Holman et al.

[11] 4,240,794

[45] Dec. 23, 1980

[54] METHOD OF PREFORMING VASCULAR GRAFTS OF HUMAN AND OTHER ANIMAL ORIGIN

[76] Inventors: Daniel G. Holman, 12743 Radisson Rd. NE., Blaine, Minn. 55434; Robert A. Ersek, 5416 Diamondhead Dr. East, Bay St. Louis, Miss. 39520; Arthur A. Beisang, 2263 Dellwood, Roseville, Minn. 55113

[21] Appl. No.: 52,068

[22] Filed: Jun. 25, 1979

Related U.S. Application Data

[63] Continuation of Ser. No. 872,605, Jan. 26, 1978, abandoned.

[51] Int. Cl.³ .................. A61L 17/00; C14C 3/08
[52] U.S. Cl. ........................ 8/94.11; 8/94.33
[58] Field of Search ............... 8/94.11, 94.33

[56] References Cited

U.S. PATENT DOCUMENTS

| | | | |
|---|---|---|---|
| 55,740 | 6/1866 | Taylor | 8/94.11 |
| 3,093,439 | 6/1963 | Bothwell | 8/94.11 |
| 3,523,027 | 8/1970 | Hall | 8/94.11 |
| 4,050,893 | 9/1977 | Hancock et al. | 8/94.11 |

OTHER PUBLICATIONS

Dardik, H. et al., *J. Amer. Medical Association,* 1976, 236, (No. 25), pp. 2859-2862.

*Primary Examiner*—A. Lionel Clingman
*Attorney, Agent, or Firm*—Orrin M. Haugen; Thomas J. Nikolai

[57] ABSTRACT

A method for preparing human and other animal unbilical cords for use as a vascular replacement and/or arterial venous fistula which permits the umbilical cord which is to be grafted to be preformed into a desired predetermined configuration. The method includes the steps of initially flushing the cord in an aqueous solution, and then mounting the flushed cord upon a mandrel having the desired configuration. The mounted cord is immersed in ethyl alcohol until substantially dehydrated and preformed, and is thereafter immersed for fixation in an aldehyde selected from the class consisting of dialdehyde starch and gluteraldehyde, with the aldehyde immersion fixing the tissue into a shape conforming to the mandrel upon which it is mounted.

3 Claims, No Drawings

METHOD OF PREFORMING VASCULAR GRAFTS OF HUMAN AND OTHER ANIMAL ORIGIN

This is a continuation of application Ser. No. 872,605 filed Jan. 26, 1978, abandoned.

BACKGROUND OF THE INVENTION

The present invention relates generally to an improved method for preparing vascular replacements and/or arterial venous fistula, and particularly wherein a preformed umbilical cord is being utilized. More specifically, the method of the present invention relates to a technique for dehydrating and thereafter fixing the umbilical cord tissue into the desired preformed configuration. Implantable prosthetic devices for either permanent or semi-permanent implantation into the body for the controlled passage of fluids are in relatively wide usage throughout the world. Normally, such implantable devices are utilized for treating renal failure through dialysis, as well as for other disorders which require replacement of arteries or veins due to damaged vessels.

In order to achieve a proper implant, the material utilized must provide for a relatively sound surface seal, the seal properly controlling or preventing the passage of fluids therearound, and furthermore providing a seal which resists infection. It has been found that processed human umbilical cords are well suited for this purpose, since processed umbilical cords are normally not rejected by the host, and furthermore, are reasonably accepted by the subcutaneous tissues of the patient.

Normally, the human umbilical cord is a relatively straight tubular member, but is, of course, highly flexible. As in any flexible tubular structure of this type, bending or forming about a relatively small radius of curvature will cause kinking or buckling of the walls, with the kink resisting flow through the cord. In accordance with the present invention, however, the umbilical cords or segments thereof may be made to conform to a predetermined configuration including relatively sharp bends through a system of dehydration followed by fixing of the structure into the desired form.

Artificial dialysis has been widely used since its development by Kolff. Since the development and demonstration of this procedure, efforts have been undertaken to improve the techniques of gaining access to the blood stream of the patient, with access being required on an intermittent and sometimes frequent basis. In the past, bovine carotid arteries have been reasonably widely used for the cannulation of blood vessels in the arterial venous systems for hemodialysis. While bovine carotid arteries are usable for such applications, it has been determined recently that human umbilical cords are preferable for certain such applications.

In an article entitled "Possible Improvements in the Technique of Long Term Cannulation of Blood Vessels" by Quinton, Dillard, Cole and Scribner, Trans. Am. Soc. for Artif. Int. Organs, 7:60, 1960, an ideal cannula for blood vessels was described having the following features:

(1) The inner surface exposed to the body fluids should minimize clotting thereof;
(2) The exterior surface should provide minimal tissue reaction so as to avoid rejection;
(3) The exterior surface should permit bonding or attachment to the skin or subcutaneous tissue;
(4) The skin should properly surround the cannula member for sealing;
(5) The cannula material should be reasonably flexible in the tissue contacting area;
(6) The cannula should be sufficiently durable so as to withstand trauma without permanent deformation;
(7) The cannula should be sufficiently flexible so as not to occlude adjacent vessels;
(8) The cannula should have a means to facilitate contact with various vessel sizes;
(9) Means should be provided to permit attachment by clamping or the like to the external circuit means when required; and
(10) The cannula should be arranged relatively close to the skin surface and not extend far into the subcutaneous tissue.

It has been found that human umbilical cords achieve most of these criteria, and are particularly well adapted to these criteria when treated in accordance with the technique of the present invention. Generally speaking, human umbilical cords, particularly when treated in accordance with the present invention, achieve a performance significantly superior to that of synthetic resinous materials, such as, for example, polyethylene terephthalate (Dacron) or the like.

SUMMARY OF THE INVENTION

Generally, and in accordance with the present invention, a human umbilical cord is arranged or conformed to a predetermined configuration by initially flushing the cord for removal of any loose tissue and other substances therefrom, and thereafter mounting the cord upon a suitable mandrel having the desired configuration, both in its axial and radial dimension. While on the mandrel, the cord is immersed in ethyl alcohol, particularly a solution having more than about 70% of ethyl alcohol, and permitted to remain immersed until substantially dehydrated, the dehydration operation normally taking at least 18 hours. Thereafter, the dehydrated cord, while remaining on the mandrel, is fixed by immersion in an aqueous solution of aldehyde selected from the group consisting of dialdehyde starch and gluteraldehyde, with the solution containing more than about 1% of the aldehyde. The fixing operation normally requires immersion for a period of about 18 hours or more.

Therefore, it is a primary object of the present invention to provide an improved implantable prosthetic device for transmission of body fluids, wherein the implantable material is a treated umbilical cord.

It is a further object of the present invention to provide an improved technique for preforming a human umbilical cord into a configuration which is required for achieving a purpose, and with the treated cord being suited for implantation within the human body.

Other and further objects of the present invention will become apparent to those skilled in the art upon a study of the following specification and appended claims.

DESCRIPTION OF THE PREFERRED EMBODIMENT

In accordance with the preferred embodiment of the present invention, a human umbilical cord is obtained and treated to achieve a desired configuration such as, for example, a configuration utilizing a straight section of approximately 10 centimeters in length, at which point a 180° bend is formed having a radius of approximately 5 centimeters. A second segment extends from the bend having a length of approximately 20 centimeters forming a J-shaped graft. Alternatively, a segment or component is formed having a straight segment of approximately 20 centimeters followed by a 180° bend with a radius of 5 centimeters, with a leg extending from the bend of approximately 20 centimeters in length forming a U-shaped graft. Such configurations are adapted for use as implants for achieving artificial dialysis on the patient when required.

As an additional alternative, a straight graft may have the internal diameter thereof gradually tapered from 8 mm. in diameter at the proximal opening to 3 mm. in diameter at the distal opening, thus allowing for more proper anostomosis with varying sized patient vessels.

In each instance, the grafts are formed by flushing with deionized water with any suitable technique, such as utilization of a flexible squeeze bottle or the like. Following flushing, the cord element is slipped upon or otherwise mounted on an appropriate mandrel having a surface with good release properties. Polished polytetrafluoroethylene has been found to provide good release qualities. The mandrel has the configuration desired, such as the J-shape described above, or a single U configuration. Alternatively, and if desired, the mandrel may be tapered to accommodate attachment to preselected members of the arterial venous system of the patient.

While mounted on the mandrel, the cord is immersed in ethyl alcohol, with the solution containing not less than 70% by volume of ethyl alcohol, with the immersion continuing for at least 18 hours. Immersion is maintained until the cord is substantially dehydrated so as to conform to the outer surface of the mandrel by shrinking thereabout, with a period of 18 hours normally being required to achieve substantial dehydration. Thereafter, the dehydrated cord, while mounted on and shrunk to the size of the mandrel is immersed in an aqueous solution of dialdehyde starch, with the solution containing not less than 1% of dialdehyde starch by volume. Fixing is achieved after immersion in the dialdehyde starch solution for a minimum of 18 hours.

All of the procedures involved may be accomplished at room temperature under normal conditions.

Thereafter, the performed cord is placed in a solution containing not less than 40% ethyl alcohol and 1% propylene oxide and stored until implanting is accomplished.

As an alternative to the above example, gluteraldehyde is substituted for the dialdehyde starch with similar results being achieved. As has been indicated, immersion in ethyl alcohol for dehydration should be in alcohol solutions containing more than 70% of ethyl alcohol by volume. Also, the aldehyde solutions should contain at least about 1% of either dialdehyde starch or gluteraldehyde. Normally, solutions of 95% alcohol and 1.3% of dialdehyde starch or gluteraldehyde are preferred.

We claim:

1. The method of conforming a human umbilical cord to a predetermined configuration for implanting in a human body which method comprises the steps of:
   (a) flushing the cord and thereafter mounting the cord upon a mandrel of the desired configuration;
   (b) initially immersing the mounted cord and manlvml into an aqueous solution of ethyl alcohol containing more than about 70% of ethyl alcohol until said cord is substantially dehydrated and shrunk onto said mandrel; and
   (c) thereafter immersing the dehydrated and mounted cord in an aqueous solution selected from the group consisting of dialdehyde starch in water and gluteraldehyde in water, wherein said solution contains more than about 1% of said aldehyde, for a period sufficiently long to permit the configuration to become fixed.

2. The method as defined in claim 1 being particularly characterized in that immersion in said ethyl alcohol solution extends for a period of at least about 18 hours.

3. The method as defined in claim 1 being particularly characterized in that said aldehyde solution contains approximately 1.3% of aldehyde in water.

* * * * *

UNITED STATES PATENT AND TRADEMARK OFFICE
CERTIFICATE OF CORRECTION

PATENT NO. : 4,240,794

DATED : December 23, 1980

INVENTOR(S) : Daniel G. Holman, Robert A. Ersek, and Arthur A. Beisang

It is certified that error appears in the above-identified patent and that said Letters Patent are hereby corrected as shown below:

Column 4, line 26, Claim 1(b) the claim reference word "manlvml" should read -- mandrel --.

Signed and Sealed this

Seventh Day of April 1981

[SEAL]

Attest:

RENE D. TEGTMEYER

Attesting Officer     Acting Commissioner of Patents and Trademarks